US006291517B1

(12) United States Patent
Bagchi et al.

(10) Patent No.: US 6,291,517 B1
(45) Date of Patent: Sep. 18, 2001

(54) METHOD FOR PREVENTING OR REDUCING STRESS-INDUCED GASTRIC INJURY USING GRAPE SEED PROANTHOCYANIDIN EXTRACT

(75) Inventors: Debasis Bagchi; Manashi Bagchi; Sidney J. Stohs, all of Omaha, NE (US)

(73) Assignee: Dry Creek Nutrition, Inc, Modesto, CA (US)

(*) Notice: Subject to any disclaimer, the term of this patent is extended or adjusted under 35 U.S.C. 154(b) by 0 days.

(21) Appl. No.: 09/444,494

(22) Filed: Nov. 19, 1999

(51) Int. Cl.[7] .......................... A61K 31/35; A61K 35/78; A61K 39/385
(52) U.S. Cl. .......................... 514/456; 514/457; 514/460; 514/925; 514/926; 514/927; 424/766
(58) Field of Search ...................................... 514/456, 457, 514/460, 925, 926, 927; 424/766

(56) References Cited

U.S. PATENT DOCUMENTS

| | | | |
|---|---|---|---|
| 4,698,360 | 10/1987 | Masquelier | 514/456 |
| 4,913,909 | 4/1990 | Hara et al. | 424/688 |
| 4,925,870 | 5/1990 | Gabetta et al. | 514/453 |
| 5,470,589 | 11/1995 | Shi | 424/698 |
| 5,912,363 | * 6/1999 | Nafisi-Movaghar et al. | 549/399 |
| 6,086,910 | 7/2000 | Howard et al. | 424/442 |
| 6,099,854 | 8/2000 | Howard et al. | 424/440 |

FOREIGN PATENT DOCUMENTS

WO9739632    10/1997   (WO) .

OTHER PUBLICATIONS

Chemical Abstracts 103:48023, "Pharmacological studies on Linderae umbellate Ramus, IV. Effects of condensed tannin related compounds on peptic activity and stress–induced gastric lesions in mice", Jan. 1985.*

Bagchi, M., et al., "Acute and Chronic Stress–Induced Oxidative Gastrointestinal Injury in Rats, and The Protective Ability Of A Novel Grape Seed Proanthocyanidin Extract," *Nutrition Research*, vol. 19, No. 8, 1189–1199 (Jun. 18, 1999).

Nguyen, P., et al., "Acute and Chronic Stress–Induced Gastrointestinal Injury in Rats, and Protection by a Novel IH636 Grape Seed Proanthocyanidin Extract (GSPE)," *Midwest Student Biomedical Research Forum*, (Feb. 19, 1999).

Banerjee, B., et al., "Grape Seed Proanthocyanidin Extract For The Treatment Of Chronic Pancreatitis," *Free Radical Biology & Medicine*, (Nov. 19, 1998).

Banerjee, B., et al., "Beneficial Effect of Grape Seed Proanthocyanidin Extract in the Treatment of Chronic Pancreatitis," *The American Journal of Gastroenterology*, vol. 93, No. 9, (Sep. 1998).

Bagchi, M. et al., "Acute and Chronic Stress–Induced Gastrointestinal Injury in Rats, and Protection By a Novel IH636 Grape Seed Proanthocyanidin Extract (GSPE)," *Free Radical Biology & Medicine*, 235 (Nov. 19, 1998).

Ye, X., et al., "The Cytotoxic Effects of a Novel IH636 Grape Seed Proanthocyanidin Extract on Cultured Human Cancer Cells," *Mol. Cell Biochem.*, 196(1–2): 99–108 (Jun. 1999).

Griffiths, DW., "The Inhibition of Digestive Enzymes by Polyphenolic Compounds," *Adv. Exp. Med. Biol.* 199:509–16 (1986).

Caderni, G., et al., "Effect of Complex Polyphenols and Colon Carcinogenesis," *Eur. J. Nutr.*, 38(3):126–32, (Jun. 1999).

Ezaki, N. et al., "Pharmacological Studies on *Linderae umbellatae* Ramus, IV. Effects of Condensed Tanin Related Compounds on Peptic Activity and Stress–Induced Gastric Lesions in Mice," *Planta Medica*, 51(1):34–38 (Feb. 1985).

* cited by examiner

*Primary Examiner*—Frederick Krass
(74) *Attorney, Agent, or Firm*—Marshall, O'Toole, Gerstein, Murray & Borun

(57) ABSTRACT

A method is disclosed for preventing and/or reducing stress-induced gastric injury by administering an amount of grape seed proanthocyanidin extract effective to inhibit injury is administered to persons identified as among those with or at risk for such injury.

11 Claims, No Drawings

METHOD FOR PREVENTING OR REDUCING STRESS-INDUCED GASTRIC INJURY USING GRAPE SEED PROANTHOCYANIDIN EXTRACT

BACKGROUND OF THE INVENTION

The invention relates generally to a method for preventing and/or treating stress-induced gastric injury in persons with a predisposition to such injury.

Gastric discomfort is a common complaint among people. In a healthy human stomach and duodenum, an effective balance exists between the potential for gastric acid and pepsin to damage gastric mucosal cells, and the ability of these cells to protect themselves from injury. Disruption of this balance has been attributed to several factors, including environmental and emotional stress, age, diet, genetics and individual behavior. This disruption is evidenced as a burning, aching or gnawing pain that may be perceived as abdominal pressure or fullness. Most of the symptoms experienced by patients under such conditions result from a breakdown of the normal mucosal defense mechanisms. Various studies have demonstrated that gastric acid and pepsin are important in the pathogenesis of dyspepsia, stomach upset, gastroesophageal reflux disease, and duodenal and gastric ulcer. Several mechanisms are believed to be important in protecting gastric and duodenal mucosa from damage by gastric acid, pepsin, bile pancreatic enzymes, as well as these external stressors/factors. These defense mechanisms include mucus, mucosal blood flow, cell renewal and bicarbonate. These factors acting in balance help maintain mucosal integrity.

Physical stress has been shown to induce significant gastrointestinal mucosal injury in animals. Water-immersion restraint stress of rats results in an increase in cell loss accompanied by an accelerated cell migration and macroscopic mucosal injury. Cell migration was found to be accelerated in fundic mucosa after 90 minutes of exposure to stress. A combination of increased cell loss and depressed epithelial proliferation may play a role in stress-related gastric lesions and injury in the rats. It has been suggested that oxygen free radicals are greatly involved in the pathogenesis of gastric injury. Free radicals may play a major role in stress-induced gastrointestinal injury.

Current treatments for gastric discomfort include administration of antacids and $H_2$-receptor antagonists. However, these treatments are not effective in preventing stress-induced gastric injury over the long term. There remains a need for an effective method to prevent and/or treat gastric injury caused by stress in persons who have or are at risk for such injury. The present invention fulfills this need and other needs, and provides further related advantages.

SUMMARY OF THE INVENTION

The present invention resides in a method to prevent and/or reduce gastric injury caused by stress. The method involves administering grape seed proanthocyanidin extract (GSPE) to a person identified to be at risk for such injury in an amount effective to prevent or reduce the injury.

Proanthocyanidins and polyphenolic bioflavonoids have demonstrated potential antioxidant and free radical scavenging ability, and have exhibited a broad spectrum of biological, pharmacological and medicinal properties. Previous studies have demonstrated that a novel IH636 GSPE is highly bioavailable to vital organs and provides significantly greater protection against biochemically generated free radicals and free radical-induced lipid peroxidation and DNA fragmentation than vitamin C, vitamin E, a combination of vitamins C plus E, and β-carotene.

The study provided as Example investigated the effects of acute and chronic stress on the enhanced production of superoxide anion, as well as lipid peroxidation, DNA fragmentation and membrane microviscosity (indices of oxidative tissue damage) in the gastric and intestinal mucosa of female Sprague-Dawley rats. Furthermore, the study determined the protective ability of GSPE against the gastrointestinal mucosal injury induced by acute and chronic stress.

Other features and advantages of the present invention should become apparent from the following detailed description of the invention, taken with the illustrative drawings, which illustrate the principles of the invention.

DESCRIPTION OF THE PREFERRED EMBODIMENT

The present invention involves administering grape seed proanthocyanidin extract (GSPE) to a person who has suffered, is at risk to suffer, or to prevent or reduce stress-induced gastric injury.

Proanthocyanidins comprise a group of polyphenolic bioflavonoids found in fruits and vegetables. They are the most common type of tannins found in fruits and vegetables, and are present in high amounts in the seeds and skins of grapes. Grape seed proanthocyanidins are natural antioxidants known to have a broad spectrum of biological, pharmacological, and chemoprotective properties against free radicals and oxidative stress. In particular, the novel GSPE, ActiVin™ IH636, is a highly bioavailable form of GSPE. High-pressure liquid chromatography-mass spectrometry and gas chromatography-mass spectrometry studies indicate that the GSPE contains monomeric- dimeric-, trimeric-, tetrameric, oligomeric-, and polymeric proanthocyanidins, as well as tannin. Proanthocyanidins and polyphenolic bioflavonoids have demonstrated potential antioxidant and free radical scavenging ability, as well as exhibit a broad spectrum of biological, pharmacological and medicinal properties. Proanthocyanidins have been the subject of considerable interest because of their broad pharmacologic activity and therapeutic potential. The biological and medicinal properties of the proanthocyanidins have been extensively reviewed.

The present invention resides in a method to prevent and/or reduce the effect of stress-induced gastric injury by administering GSPE to a person identified to be at risk for such injury, in an amount effective to prevent or reduce the injury. To determine the effectiveness of GSPE in this method, the effects of acute and chronic stress on the enhanced production of superoxide anion, as well as lipid peroxidation, DNA fragmentation and membrane microviscosity (indices of oxidative tissue damage) in the gastric and intestinal mucosa of female Sprague-Dawley rats were investigated, and the protective ability of GSPE was determined against the gastrointestinal mucosal injury induced by acute and chronic stress.

EXAMPLE

1. Animals and Treatment

Female Sprague-Dawley rats (160–180 g) were obtained from Sasco (Omaha, Nebr.). The animals were housed in a controlled environment at 25° C. with a 12-hour light and a 12-hour dark cycle, and were acclimated for 3–5 days before use. Unless otherwise stated, all animals were allowed free access to food (Purina Rodent Lab Chow No. 5001) and tap water. A protocol entitled "Restraint Stress, Diet, and Chemically-induced Oxidative Stress in Rats, and the Protective . . ." (ARC #0295) was approved by the Creighton University Animal Research Committee for this project. GSPE solution was freshly prepared daily for this study.

Acute and chronic restraint stress was induced by water immersion (water temperature of 23° C.) in a water tank measuring 30 cm ×45 cm, with water depth of approximately 11.5 cm, as described by Kuwayama et al., Effects of Water Immersion Restraint Stress on Rat Gastric Epithelial Cell Loss and Migration, *J. Clin. Gastroenterol.,* 10 (Suppl. 1): S78–S83, 1988. The movements of these animals were not restrained. During this process, the animals were highly stressed because they could not support themselves by standing on the bottom or grasping onto the side of the tank.

Acute stress was induced in the rats for 90 minutes as described by Kuwayama et al. Half of the rats received GSPE (100 mg/kg/day) for 15 consecutive days prior to exposure to acute 90 minute water-immersion restraint stress on the fifteenth day. Animals were sacrificed after the fifteenth day of exposure to stress.

Chronic stress was induced in the rats for 15 minutes per day for 15 consecutive days as described by Kuwayama et al. The rats were exposed daily to chronic stress after an overnight fast. Half of the rats were given GSPE (100 mg/kg/day) for 15 consecutive days, 30–45 minutes prior to the exposure to the chronic water-immersion restraint stress. The rats were sacrificed by decapitation after the 15th day of exposure to stress. The gastric and intestinal mucosa were isolated from the rats using methods described in Heylings, Gastrointestinal Absorption of Paraquat in the Isolated Mucosa of the Rat, *Toxicol. Appl. Pharmacol.,* 107: 482–493, 1991.

2. Chemicals

A commercially available dried, powdered IH636 GSPE (batch no. AV 609016) was obtained from InterHealth Nutraceuticals Incorporated (Concord, Calif.). All other chemicals and supplies used in this study were obtained from Sigma Chemical Co. (St. Louis, Mo.), and were of analytical grade or the highest grade available.

3. Lipid Peroxidation

The formation of thiobarbituric acid reactive substances (TBARS) associated with gastric and intestinal mucosa from control and treated animals was determined as an index of lipid peroxidation according to the method described in Buege and Aust, Microsomal Lipid Peroxidation, *Meth. Enzymol.,* 52: 302–310, 1978. Malondialdehyde was used as the standard. Absorbance values were measured at 535 nm, and an extinction coefficient of $1.56 \times 10^5 M^{-1} cm^{-1}$ was used.

4. DNA Fragmentation

Frozen gastric and intestinal mucosa samples were homogenized in a lysis buffer (5 mM Tris-HCl, 20 mM EDTA, 0.5% Triton X-100, pH 8.0). Homogenates were centrifuged at 27,000 ×g for 20 min to separate intact chromatin in the pellets from fragmented DNA in the supernatant fractions. Pellets were resuspended in 0.5 N perchloric acid. 5.5 N perchloric acid was added to supernatant fractions to reach a concentration of 0.5 N. Samples were heated at 90° C. for 15 minutes and centrifuged at 1,500 ×g for 10 min to remove protein. Resulting supernatant fractions were reacted with diphenylamine for 16–20 hours at room temperature. Absorbance was measured at 600 nm. DNA fragmentation in the control samples is expressed as a percentage of total DNA appearing in the supernatant fraction. Treatment effects are reported as percent of control fragmentation.

5. Membrane Microviscosity

The microviscosity of the gastric mucosa and intestinal mucosa from control and treated animals was determined as described previously. The samples were treated with 0.5 mM diphenylhexatriene (DPH) in tetrahydrofuran as the fluorescent probe and incubated for 2 hours at 37° C. as has been previously published. Fluorescence polarization as a measure of membrane microviscosity was determined at 25° C. using a thermostated cuvette holder in a Perkin-Elmer spectrofluorometer equipped with perpendicular and parallel polarizers and an excitation wavelength of 365 nm and an emission wavelength of 430 nm. Fluorescence polarization and the apparent microviscosity were calculated as described in Shintzky and Barrenholz, Fluidity Parameters of Lipid Regions Determined by Fluorescence Polarization, *Biochim. Biophys. Acta.,* 515: 367–394, 1978.

6. Cytochrome c Reduction

Superoxide anion production was measured by the assay method of Babior et al., Production of Leukocytes of Superoxide: A Potential Bactericidal Agent, *J. Clin. Invest.,* 52: 741–744, 1973, which is based on the reduction of cytochrome c. In 1.0 mL, the reaction mixtures contained 1 mg protein and 0.05 mM cytochrome c in the incubation buffer. The incubation mixtures were incubated for 15 minutes at 37° C. The reactions were terminated by placing the reaction mixtures on ice. The mixtures were centrifuged for 10 minutes, and the supernatant fractions were transferred to clean tubes for spectrophotometric measurement at 550 nm. Absorbance values were converted to nmol of cytochrome c reduced/ 15 min/mg of protein using the extinction coefficient $2.1 \times 10^4 M^{-1} cm^{-1}$.

7. Statistical Methods

The presence of significant differences between mean values was determined using Student's t test or by Analysis of Variance (ANOVA) followed by Scheffe's S method as the post hoc test. Each value is the mean ±standard deviation of the results from 4–6 experiments. The level of statistical significance in all cases was $p < 0.05$.

RESULTS

1. Stress-Induced Gastrointestinal Mucosal Lipid Peroxidation and Protection by GSPE Since lipid peroxidation occurs in response to free radicals and oxidative stress, the in vivo effects of acute and chronic stress were assessed on both gastric and intestinal mucosa. The production of thiobarbituric acid reactive substances (TBARS) as an index of lipid peroxidation is presented in Table 1. The results demonstrate that acute and chronic stress increased mucosal lipid peroxidation by approximately 3.3- and 2.9-fold in the gastric mucosa, and 4.4- and 3.3-fold in the intestinal mucosa, respectively, as compared to the control animals. Thus, acute and chronic stress increased mucosal lipid peroxidation by approximately 330% and 290% in the gastric mucosa, and 440% and 330% in the intestinal mucosa, respectively, as compared to the control animals.

Following administration of GSPE alone for 15 days to the rats, gastric and intestinal mucosal lipid peroxidation increased by approximately 1.3- and 1.5-fold, respectively, as compared to control animals. In other words, GSPE treatment alone increased gastric and intestinal mucosal lipid peroxidation by approximately 30% and 50%, respectively, as compared to the control animals. Slight increases in mucosal lipid peroxidation was observed in GSPE-treated groups following an overnight fast, which is expected following consumption of food and/or beverage. Gastrointestinal lesions were observed in animals exposed to both acute and chronic stress. No lesions occurred in the GSPE-treated animals. Pretreatment of the rats with GSPE decreased acute and chronic stress-induced lipid peroxidation by approximately 15.3% and 22.8% in the gastric mucosa, and 13.4% and 26.3% in the intestinal mucosa, respectively, as compared to non-GSPE-treated groups.

TABLE 1

Acute and Chronic Stress-induced Lipid Peroxidation (TBARS content nmol/mg protein) in the Gastric and Intestinal Mucosa of Rats and the Protective Ability of GSPE

| Animal Group | Lipid Peroxidation (TBARS Content nmol/mg protein) | |
| --- | --- | --- |
| | Gastric Mucosa | Intestinal Mucosa |
| 1. Control group | $1.80 \pm 0.29^a$ | $1.20 \pm 0.16^a$ |
| 2. GSPE-treated group (15 days) | $2.33 \pm 0.31^b$ | $1.84 \pm 0.22^b$ |
| 3. Acute Stress | $5.95 \pm 0.25^c$ | $5.22 \pm 0.33^c$ |
| 4. Acute Stress + GSPE | $5.04 \pm 0.44^d$ | $4.52 \pm 0.25^d$ |
| 5. Chronic Stress | $5.22 \pm 0.30^d$ | $3.95 \pm 0.29^e$ |
| 6. Chronic Stress + GSPE | $4.03 \pm 0.24^e$ | $2.91 \pm 0.23^f$ |

Each value in Table 1 is the mean ±standard deviation of results from 4–6 animals. Malondialdehyde was used as the standard. Values with non-identical superscripts are significantly different (i.e., with $p < 0.05$).

2. Acute and Chronic Stress-Induced DNA Fragmentation in the Gastric and Intestinal Mucosa, and Protection by GSPE DNA fragmentation in the gastric and intestinal mucosa induced by acute and chronic stress was determined as an index of oxidative DNA damage. These results are shown in Table 2. Approximately 4.1- and 3.3-fold increases in DNA fragmentation were observed in the gastric mucosa following exposure to acute and chronic stress, respectively, while under these same conditions approximately 5.2- and 4.2-fold increases in DNA fragmentation were observed in the intestinal mucosa, respectively, as compared to control animals. Thus, acute and chronic stress increased mucosal DNA fragmentation by approximately 410% and 330% in the gastric mucosa, and 520% and 420% in the intestinal mucosa, respectively, as compared to the control animals.

Following administration of GSPE alone for 15 days, DNA fragmentation increased by 1.3- and 1.7-fold in the gastric and intestinal mucosa, respectively as compared to non-GSPE treatment groups. In other words, GSPE treatment alone increased gastric and intestinal mucosal DNA fragmentation by approximately 30% and 70%, respectively, as compared to the control animals. Slight increases in mucosal DNA fragmentation in GSPE-treated groups following overnight fast is expected following consumption of food and/or beverage. Pretreatment of rats with GSPE decreased acute and chronic stress-induced DNA fragmentation by 12% and 21% in the gastric mucosa, respectively, and approximately 14% and 26% in the intestinal mucosa, respectively, as compared to non-GSPE-treated groups.

TABLE 2

Acute and Chronic Stress-Induced DNA Fragmentation in the Gastric and Intestinal Mucosa and the Protective Ability of GSPE

| Animal Group | Gastric Mucosa | Intestinal Mucosa |
| --- | --- | --- |
| 1. Control group | $4.35 \pm 0.23^a$ | $3.48 \pm 0.29^a$ |
| 2. GSPE-treated group (15 days) | $5.65 \pm 0.48^b$ | $5.79 \pm 0.41^b$ |
| 3. Acute Stress | $17.66 \pm 1.57^c$ | $18.01 \pm 1.39^c$ |
| 4. Acute Stress + GSPE | $15.54 \pm 2.91^d$ | $15.47 \pm 3.96^d$ |

TABLE 2-continued

Acute and Chronic Stress-Induced DNA Fragmentation in the Gastric and Intestinal Mucosa and the Protective Ability of GSPE

| Animal Group | Gastric Mucosa | Intestinal Mucosa |
| --- | --- | --- |
| 5. Chronic Stress | $14.36 \pm 2.42^e$ | $14.62 \pm 1.80^e$ |
| 6. Chronic Stress + GSPE | $11.31 \pm 1.56^f$ | $10.78 \pm 1.13^f$ |

Each value in Table 2 is the mean ±standard deviation of results from 4–6 animals. Values with non-identical superscripts are significantly different (i.e., with $p < 0.05$).

3. Modulation of Membrane Microviscosities in the Gastrointestinal Mucosa of Rats Following Exposure to Stress, and Protection by GSPE Membrane microviscosity was determined as an index of membrane integrity. Membrane microviscosity is inversely proportional to membrane fluidity. The changes in membrane fluidity occur due to the direct effect of these stressors on the structural integrity of the gastric and intestinal mucosa, including the changes in lipid peroxidation. The effects of these necrotizing agents on the membrane microviscosity of gastric and intestinal mucosa are shown in Table 3. Acute and chronic stress increased membrane microviscosities by 11.6- and 6.3-fold in the gastric mucosa, respectively, and approximately 16.6- and 9.3-fold in the intestinal mucosa, respectively, as compared to control animals. Thus, acute and chronic stress increased mucosal membrane microviscosity by approximately 1160% and 630% in the gastric mucosa, and 1660% and 930% in the intestinal mucosa, respectively, as compared to the control animals.

Following administration of GSPE for 15 days, membrane microviscosities increased in the gastric and intestinal mucosa by approximately 1.5- and 1–3 fold, respectively, as compared to control animals. In other words, GSPE treatment alone increased gastric and intestinal mucosal membrane microviscosity by approximately 50% and 30%, respectively, as compared to the control animals. Small increases in mucosal membrane microviscosities were observed in GSPE-treated groups following overnight fast, which is expected following consumption of food and/or beverage. Pretreatment of the rats with GSPE decreased acute and chronic stress-induced membrane microviscosities by 13% and 25% in the gastric mucosa, respectively, and approximately by 16% and 25% in the intestinal mucosa, respectively, as compared to non-GSPE-treated groups.

TABLE 3

Acute and Chronic Stress-Induced Modulation of Membrane Microviscosities (in poise) in the Gastric and Intestinal Mucosa, and the Protective Ability of GSPE

| Animal Group | Membrane Microviscosity (in poise) | |
| --- | --- | --- |
| | Gastric Mucosa | Intestinal Mucosa |
| 1. Control group | $0.16 + 0.03^a$ | $0.11 + 0.02^a$ |
| 2. GSPE (15 days) | $0.24 + 0.05^b$ | $0.14 + 0.03^a$ |
| 3. Acute Stress | $1.86 + 0.22^c$ | $1.83 + 0.40^b$ |
| 4. Acute Stress + GSPE | $1.62 + 0.32^d$ | $1.54 + 0.28^c$ |
| 5. Chronic Stress | $1.00 + 0.13^e$ | $1.02 + 0.18^d$ |
| 6. Chronic Stress + GSPE | $0.75 + 0.09^f$ | $0.77 + 0.10^e$ |

Each value in Table 3 is the mean ±standard deviation of results from 4–6 animals. Values with non-identical superscripts are significantly different (i.e., with $p < 0.05$).

4. Enhanced Production of Superoxide Anion in the Gastric and Intestinal Mucosa of Rats Following Exposure to Acute and Chronic Stress, and Protection by GSPE The production of superoxide anion in the gastric and intestinal mucosa following induction of acute and chronic stress was assessed by cytochrome c reduction. The results of cytochrome c reduction in gastric and intestinal mucosa are presented in Table 4. Approximately 12.2- and 4.8-fold increases in cytochrome c reduction were observed in gastric mucosa, following exposure to acute and chronic stress, respectively, while under these same conditions 12.1- and 4.6-fold increases in cytochrome c reduction were observed in the intestinal mucosa, respectively, as compared to the control animals. Thus, acute and chronic stress increased mucosal superoxide anion production (as determined by cytochrome c reduction) by approximately 1220% and 480% in the gastric mucosa, and 1210% and 460% in the intestinal mucosa, respectively, as compared to the control animals.

Following administration of GSPE (100 mg/kg/day) for 15 days, approximately 1.2- and 1.0-fold increases in cytochrome c reduction were observed in the gastric and intestinal mucosa, respectively. In other words, GSPE treatment alone increased gastric and intestinal mucosal superoxide anion production (as determined by cytochrome c reduction) by approximately 20% and 0%, respectively, as compared to the control animals. Pretreatment of the rats with GSPE descreased acute and chronic stress-induced cytochrome c reduction by approximately 17.2% and 24.4% in the gastric mucosa, and 18.7% and 26.3% in the intestinal mucosa, respectively, as compared to non-GSPE-treated groups.

TABLE 4

Stress-Induced Production of Superoxide Anion (Cytochrome c Reduction) in the Gastric and Intestinal Mucosa, and the Protective Ability of GSPE

| Animal Group | nmol cytochrome c reduced/15 min/m.g. of protein | |
|---|---|---|
| | Gastric Mucosa | Intestinal Mucosa |
| 1. Control group | $22.64 + 2.61^a$ | $22.80 + 1.35^a$ |
| 2. GSPF (15 days) | $27.20 + 3.71^b$ | $20.93 + 3.48^a$ |
| 3. Acute Stress | $276.4 + 13.7^c$ | $276.5 + 20.9^b$ |
| 4. Acute Stress + GSPE | $228.56 + 23.82^d$ | $224.71 \pm 24.34^c$ |
| 5. Chronic Stress | $108.68 + 9.36^e$ | $1.04 + 11.02^d$ |
| 6. Chronic Stress + GSPE | $82.16 \pm 14.21^f$ | $77.31 \pm 9.37^e$ |

Each value in Table 4 is the mean ±standard deviation of results from 4–6 animals. Values with non-identical superscripts are significantly different (i.e., with $p<0.05$).

Discussion

The major objective of the study presented was to assess the role of reactive oxygen species on the induction of oxidative gastrointestinal mucosal injury in rats following exposure to acute and chronic stress, and the protective ability of GSPE. Sprague-Dawley rats were exposed to acute and chronic stress after which the production of reactive oxygen species and the extent of membrane and DNA damage in the gastric and intestinal mucosa were assessed. Furthermore, the gastroprotective ability of a novel free radical scavenger and antioxidant GSPE was determined against acute and chronic stress.

The present studies have assessed the protective ability of GSPE against acute and chronic stress-induced gastrointestinal injury. Kuyayama et al. have demonstrated that water-immersion restraint stress in rats resulted in an increase in cell loss in the gastrointestinal tract and macroscopic mucosal injury. This combination of increased cell loss with depressed epithelial proliferation may play a role in stress-related gastric lesions and injury in rats.

These studies demonstrated enhanced production of oxygen free radicals including superoxide anion in the gastric and intestinal mucosa in vivo following exposure to acute and chronic stress. Since lipid peroxidation occurs in response to free radicals and reactive oxygen species, the in vivo effects of acute and chronic stress were assessed on both gastric and intestinal mucosa. Enhanced production of superoxide anion in these tissues was determined by cytochrome c reduction, while oxidative tissue damage was determined by quantitating lipid peroxidation, DNA fragmentation and membrane microviscosity. Lipid peroxidation was assessed as an index of oxidative lipid degradation induced by acute and chronic stress. Programmed cell death, morphologically known as apoptosis, is a selective process of physiological cell deletion that plays a major role in developmental biology and in maintenance of homeostasis in vertebrates. Apoptosis is accompanied by condensation of cytoplasm, loss of plasma membrane microvilli, condensation and fragmentation of nuclei, and extensive degradation of chromosomal DNA. Thus, DNA fragmentation was quantitated and correlated with oxidative stress. Membrane microviscosity is inversely proportional to the membrane fluidity. The changes in membrane fluidity occur due to the direct effect of these stressors on the structural integrity of the gastric and intestinal mucosa, including the changes in lipid peroxidation. Slight increases in mucosal lipid peroxidation, DNA fragmentation and membrane microviscosities were observed in GSPE-treated groups following overnight fast, which is expected following consumption of food and/or beverage.

In summary, the results of these experiments clearly demonstrate that reactive oxygen species including superoxide anion, are involved in the pathogenesis of acute and chronic stress-induced gastrointestinal injury, and can result in enhanced lipid peroxidation, increased DNA fragmentation and altered membrane fluidity. GSPE demonstrated significant protective ability against chronic stress-induced gastrointestinal mucosal injury, and some protection against acute stress.

In view of these results, administering GSPE to patients who are at risk for stress-induced gastric reperfusion injury will serve as an effective method for prevention of such injury. Administration of GSPE prior to onset of stress or as a regular supplement is believed to be most effective in helping to prevent such injury.

The method involves identification of those prone to such injury, preferably by a physician. These persons would likely be those with a history of gastric injury, or those regularly exposed to high levels of stress. Existing gastric injury, such as an ulcer, can be identified through its symptom, and also determined by use of endoscopy and ultrasound.

Next, GSPE is administered to these identified persons in an amount sufficient to prevent or reduce the stress-induced gastric injury. Though the preferred method of administration is oral, various known methods for administering compounds to a person would also be effective, such as intravenously or intramuscularly. In the study previously detailed, 100 mg/day per kg of body weight was found to be effective in reducing stress-induced gastric injury in rats. This is equivalent to a dose of 164 mg of GSPE per day for a 70 kg adult human. Based on these results and other in vivo studies, a preferred daily dose to prevent injury is roughly 100–200 mg of GSPE, preferably in two equally divided doses taken within 15 to 30 minutes after meals. If GSPE is taken after, rather than prior to, onset of stress, a somewhat higher dose may be required to be effective. Such post-stress use will likely not be as effective as regular supplementation with GSPE.

Although the invention has been disclosed in detail with reference only to the preferred embodiments, those skilled in the art will appreciate that additional methods of administering GSPE can be made without departing from the scope of the invention. Accordingly, the invention is defined only by the following claims.

We claim:

1. A method for preventing or reducing stress-induced gastric injury in a person at risk for such injury, the method comprising:

identifying a person with or at risk for such injury; and administering grape seed proanthocyanidin extract to the person in an amount effective to prevent or reduce the injury.

2. A method as defined in claim 1, wherein:

the person is an adult; and the amount of grape seed proanthocyanidin extract administered is from about 100 to about 200 mg/day.

3. A method as defined in claim 1, wherein the step of administering grape seed proanthocyanidin extract occurs twice daily, a time after the person has eaten.

4. A method as defined in claim 1, wherein the step of identifying a person at risk for such injury includes determination by a physician of existence or risk of stress-induced gastric injury in the person.

5. A method as defined in claim 1, wherein the step of administering grape seed proanthocyanidin extract is performed orally.

6. A method as defined in claim 1, wherein the step of administering grape seed proanthocyanidin extract is performed intravenously.

7. A method as defined in claim 1, wherein the step of administering grape seed proanthocyanidin extract is performed intramuscularly.

8. A method for preventing or reducing stress-induced gastric injury in an adult with or at risk for such injury, the method comprising:

identifying an adult at risk for such injury; and orally administering grape seed proanthocyanidin extract to the person in an amount effective to prevent or reduce the injury, the amount being about 100 to about 200 mg of grape seed proanthocyanidin extract per day.

9. A method for preventing or reducing stress-induced gastric injury in a person with or at risk for such injury, the method comprising administering to the person grape seed proanthocyanidin extract in an amount effective to prevent or reduce such injury.

10. A method as defined in claim 9, wherein:

the person is an adult; and the amount of grape seed proanthocyanidin extract administered in the step of administering ranges from about 100 to about 200 mg/day.

11. A method as defined in claim 9, wherein the step of administering grape seed proanthocyanidin extract occurs twice daily, after the person has eaten.

* * * * *